(12) United States Patent
Schmidt (10) Patent No.: US 10,569,746 B2
(45) Date of Patent: Feb. 25, 2020

(54) SENSOR CLEANING SYSTEM

(71) Applicant: Ford Global Technologies, LLC, Dearborn, MI (US)

(72) Inventor: David Schmidt, Dearborn, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 212 days.

(21) Appl. No.: 15/458,236

(22) Filed: Mar. 14, 2017

(65) Prior Publication Data

US 2018/0265048 A1    Sep. 20, 2018

(51) Int. Cl.
| | |
|---|---|
| *B08B 1/00* | (2006.01) |
| *B60S 1/56* | (2006.01) |
| *B08B 3/02* | (2006.01) |
| *B08B 5/02* | (2006.01) |
| *B60S 1/46* | (2006.01) |
| *B60S 1/54* | (2006.01) |
| *G01S 17/93* | (2020.01) |

(52) U.S. Cl.
CPC .............. *B60S 1/566* (2013.01); *B08B 1/002* (2013.01); *B08B 1/006* (2013.01); *B08B 3/02* (2013.01); *B08B 5/02* (2013.01); *B60S 1/46* (2013.01); *B60S 1/542* (2013.01); *G01S 17/936* (2013.01); *B60Y 2400/30* (2013.01)

(58) Field of Classification Search
CPC .. B60S 1/566; B60S 1/46; B60S 1/542; B60S 1/0818; B08B 1/002; B08B 1/005; B08B 1/006; B08B 3/02; B08B 5/02; B08B 13/00; G01N 21/15; G01N 21/534; G01N 2021/151; G01N 2021/152; G01N 2021/157; G01N 2021/1793; G01S 17/023; G01S 17/936; G01S 2007/4977; B60Y 2400/30
USPC ....................................................... 134/56 R
See application file for complete search history.

(56) References Cited

U.S. PATENT DOCUMENTS

| | | | |
|---|---|---|---|
| 7,839,491 B2 | 11/2010 | Harris et al. | |
| 8,139,109 B2 | 3/2012 | Schmiedel et al. | |
| 2002/0139394 A1 | 10/2002 | Bronson | |
| 2008/0210881 A1* | 9/2008 | Harris ..................... | G01S 17/95 250/393 |

(Continued)

FOREIGN PATENT DOCUMENTS

| | | |
|---|---|---|
| DE | 10332939 B4 | 8/2011 |
| DE | 102016006039 A1 | 11/2016 |

(Continued)

OTHER PUBLICATIONS

EP1304583B1—machine translation (Year: 2006).*

(Continued)

*Primary Examiner* — Michael E Barr
*Assistant Examiner* — Tinsae B Ayalew
(74) *Attorney, Agent, or Firm* — Frank A. MacKenzie; Bejin Bieneman PLC (57) ABSTRACT

A system includes a sensor base, a sensor cover having a window that is rotatably mounted to the base. The system includes a contacting cleaner and a contactless cleaner. The system further includes a processor that is programmed to actuate, first, the contactless cleaner and, then, upon determining that opacity of the window exceeds a predetermined threshold after actuation of the contactless cleaner, the contacting cleaner.

17 Claims, 6 Drawing Sheets

(56) References Cited

U.S. PATENT DOCUMENTS

2014/0007909 A1    1/2014    Manaois et al.
2015/0036037 A1    2/2015    Glenn
2016/0244028 A1*  8/2016    Wakatsuki .............. B60S 1/566

FOREIGN PATENT DOCUMENTS

EP              1304583 A2    4/2003
WO    WO 2013087799 A4    6/2013
WO    WO 2015120866 A1    8/2015

OTHER PUBLICATIONS

Search Report dated Jul. 5, 2018 from the United Kingdom Intellectual Property Office regarding Application No. GB1803837.2 (3 pages).

* cited by examiner

SENSOR CLEANING SYSTEM

BACKGROUND

A vehicle may include one or more object detection sensors such as Light Detection and Ranging (LIDAR) sensors to detect objects, e.g., in an area outside the vehicle. A sensor for detecting objects outside a vehicle may be mounted to a vehicle exterior. For example, a sensor may be mounted to a vehicle roof, pillar, etc. A sensor such as a LIDAR sensor is typically subject to environmental conditions, e.g., dirt, dust, etc., that can impair operation of the sensor.

DETAILED DESCRIPTION

Introduction

Disclosed here in a system including a sensor base, a sensor cover including a window that is rotatably mounted to the base, a contacting cleaner, and a contactless cleaner. The system further includes a processor that is programmed to actuate the contactless cleaner. The processor is further programmed to then actuate the contacting cleaner upon determining that opacity of the window exceeds a predetermined threshold after actuation of the contactless cleaner.

The contactless cleaner may further include an air nozzle directed to the window.

The contactless cleaner may further include a cleaning fluid spray nozzle directed to the window.

The contacting cleaner may include a wiper mechanically connected to an actuator. The processor may be further programmed to actuate the actuator to move the wiper to a window contacting position.

The contacting cleaner may have a contactless position and a window contacting position, and the contacting cleaner physically touches the window in a window contacting position.

An electromechanical actuator may be mechanically coupled to the contacting cleaner, and the processor may be further programmed to actuate the electromechanical actuator to move the contacting cleaner from the contactless position to the window contacting position.

The contactless cleaner may be a first contactless cleaner and the system may further include a second contactless cleaner, and the processor is further programmed to actuate the first contactless cleaner, and then actuate the second contactless cleaner upon determining that the opacity of the window exceeds a predetermined threshold after actuation of the first contactless cleaner.

The system may further include an electromechanical actuator mechanically coupled to the contacting cleaner, wherein the processor is further programmed to actuate the electromechanical actuator to move the contacting cleaner from the contactless position to the window contacting position.

The processor may be further programmed to actuate the second contactless cleaner upon determining that the opacity of the window exceeds a predetermined threshold after actuation of the first contactless cleaner for a predetermined time.

The system may further include a cleaning arm mounted to the sensor base, wherein the contactless and the contacting cleaners are mounted to the cleaning arm.

The processor may be further programmed to determine a change in a rotational speed of the cover upon actuation of the contacting cleaner, and cause an adjustment to interpretation of data from the sensor according to the changed rotational speed.

The processor may be further programmed to deactivate a sensor excitation source upon actuation of the contacting cleaner.

The processor may be further programmed to actuate the contacting cleaner based at least in part on a rotational position of the window.

Further disclosed herein is a method that includes actuating a contactless cleaner of a sensor window, and upon determining that opacity of the window exceeds a predetermined threshold after actuation of the contactless cleaner, actuating a contacting cleaner.

The method may further include actuating an electromechanical actuator to move the contacting cleaner from a contactless position to a window contacting position.

The method may further include actuating the contactless cleaner, and then actuating a second contactless cleaner upon determining that the opacity of the window exceeds a predetermined threshold after actuation of the contactless cleaner. Actuating of the second contactless cleaner may be performed only upon determining that the opacity of the window exceeds a predetermined threshold after actuation of the first contactless cleaner for a predetermined time.

The method may further include determining a change in a rotational speed of the cover upon actuation of the contacting cleaner, and causing an adjustment to interpretation of data from the sensor according to the changed rotational speed.

The method may further include deactivating a sensor excitation source upon actuation of the contacting cleaner.

The method may further include actuating the contacting cleaner based at least in part on a rotational position of the window.

Further disclosed is a computing device programmed to execute the any of the above method steps.

Yet further disclosed is a computer program product, comprising a computer readable medium storing instructions executable by a computer processor, to execute any of the above method steps.

Exemplary System Elements

Figure 1:
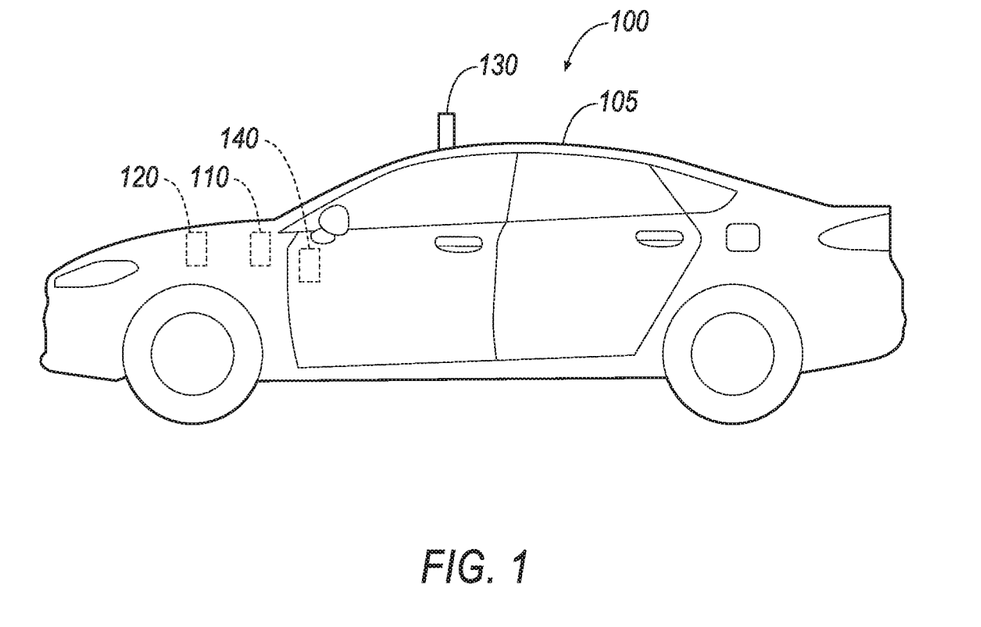
FIG. 1 is a diagram illustrating an example vehicle.

FIG. 1 illustrates a vehicle 100. The vehicle 100 may be powered in a variety of known ways, e.g., with an electric motor and/or internal combustion engine. The vehicle 100 may be a land vehicle such as a car, truck, etc. A vehicle 100 may include a computer 110, actuator(s) 120, sensor(s) 130, and a human machine interface (HMI) 140.

The computer 110 includes a processor and a memory such as are known. The memory includes one or more forms of computer-readable media, and stores instructions executable by the computer 110 for performing various operations, including as disclosed herein.

The computer 110 may operate the vehicle 100 in an autonomous mode, a semi-autonomous mode, or a non-autonomous mode. For purposes of this disclosure, an autonomous mode is defined as one in which each of vehicle 100 propulsion, braking, and steering are controlled by the computer 110; in a semi-autonomous mode the computer 110 controls one or two of vehicles 100 propulsion, braking, and steering; in a non-autonomous mode, an operator controls the vehicle 100 propulsion, braking, and steering.

The computer 110 may include programming to operate one or more of land vehicle brakes, propulsion (e.g., control of acceleration in the vehicle by controlling one or more of an internal combustion engine, electric motor, hybrid engine, etc.), steering, climate control, interior and/or exterior lights, etc., as well as to determine whether and when the computer 110, as opposed to a human operator, is to control such operations. Additionally, the computer 110 may be programmed to determine whether and when a human operator is to control such operations.

The computer 110 may include or be communicatively coupled to, e.g., via a vehicle 100 communications bus as described further below, more than one processor, e.g., controllers or the like included in the vehicle for monitoring and/or controlling various vehicle controllers, e.g., a powertrain controller, a brake controller, a steering controller, etc. The computer 110 is generally arranged for communications on a vehicle communication network that can include a bus in the vehicle such as a controller area network (CAN) or the like, and/or other wired and/or wireless mechanisms.

Via the vehicle 100 network, the computer 110 may transmit messages to various devices in the vehicle and/or receive messages from the various devices, e.g., an actuator 120, an HMI 140, etc. Alternatively or additionally, in cases where the computer 110 actually comprises multiple devices, the vehicle 100 communication network may be used for communications between devices represented as the computer 110 in this disclosure. As discussed further below, various electronic controllers and/or sensors 130 may provide data to the computer 110 via the vehicle communication network.

The vehicle 100 actuators 120 are implemented via circuits, chips, or other electronic and/or mechanical components that can actuate various vehicle subsystems in accordance with appropriate control signals, as is known. The actuators 120 may be used to control vehicle 100 systems such as braking, acceleration, and/or steering of the vehicles 100.

Vehicle 100 sensors 130 may include a variety of devices known to provide data via the vehicle communications bus. For example, the sensors 130 may include one or more camera, radar, infrared, and/or LIDAR sensors 130 disposed in the vehicle 100 and/or on the vehicle 100 providing data encompassing at least some of the vehicle 100 exterior. The data may be received by the computer 110 through a suitable interface such as is known. A LIDAR sensor 130 disposed, e.g., on a roof 105, pillar, etc., of the vehicle 100, may provide object data including relative locations, sizes, and shapes of objects such as other vehicles surrounding the vehicle 100. A vehicle 100 computer 110 may receive the object data and operate the vehicle in an autonomous and/or semi-autonomous mode based at least in part on the received object data.

The HMI 140 may be configured to receive user input, e.g., during operation of the vehicle 100. For example, a user may select a mode of operation, e.g., an autonomous mode, by inputting a requested mode of operation via a HMI 140. Moreover, a HMI 140 may be configured to present information to the user. Thus, a HMI 140 may be located in a passenger compartment of the vehicle 100. In an example, the computer 110 may output information indicating that a vehicle 100 mode of operation such as an autonomous mode is deactivated due to an event, e.g., a LIDAR sensor 130 sensor blockage that impairs its object detection operation.

Figure 2A:
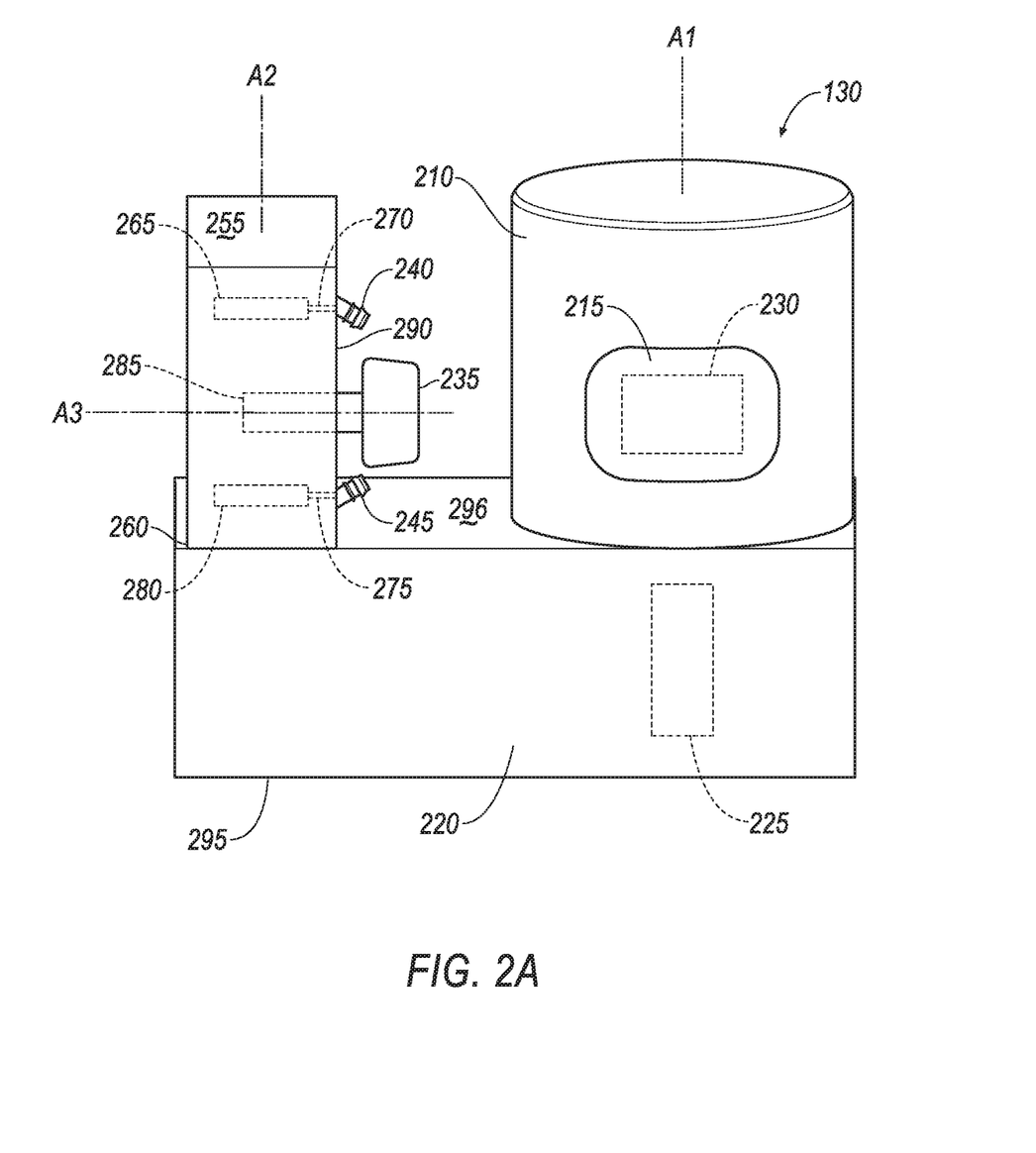
FIG. 2A is a diagram showing a side view of the example sensor assembly including contacting and contactless cleaners.
Figure 2B:
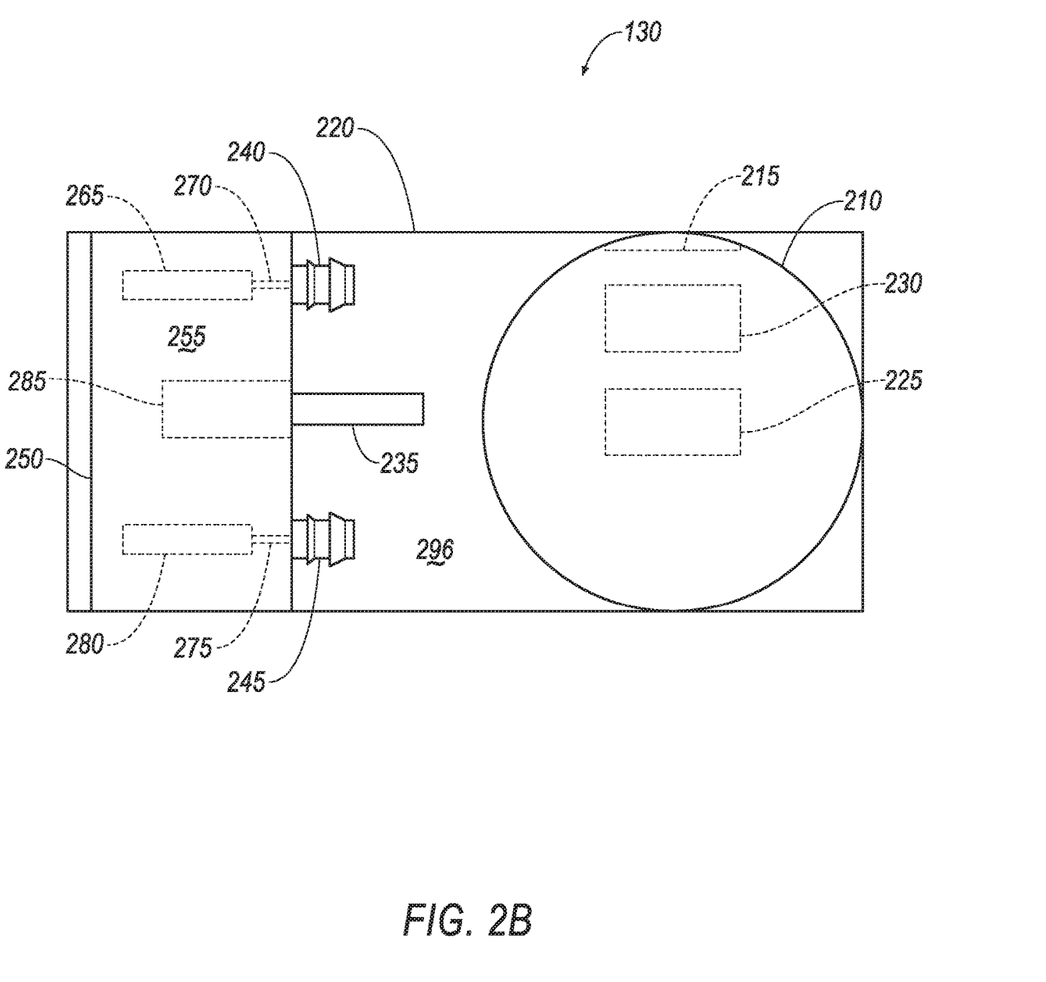
FIG. 2B is a diagram showing a top view of the sensor assembly with the contacting cleaner in a contactless position.
Figure 2C:
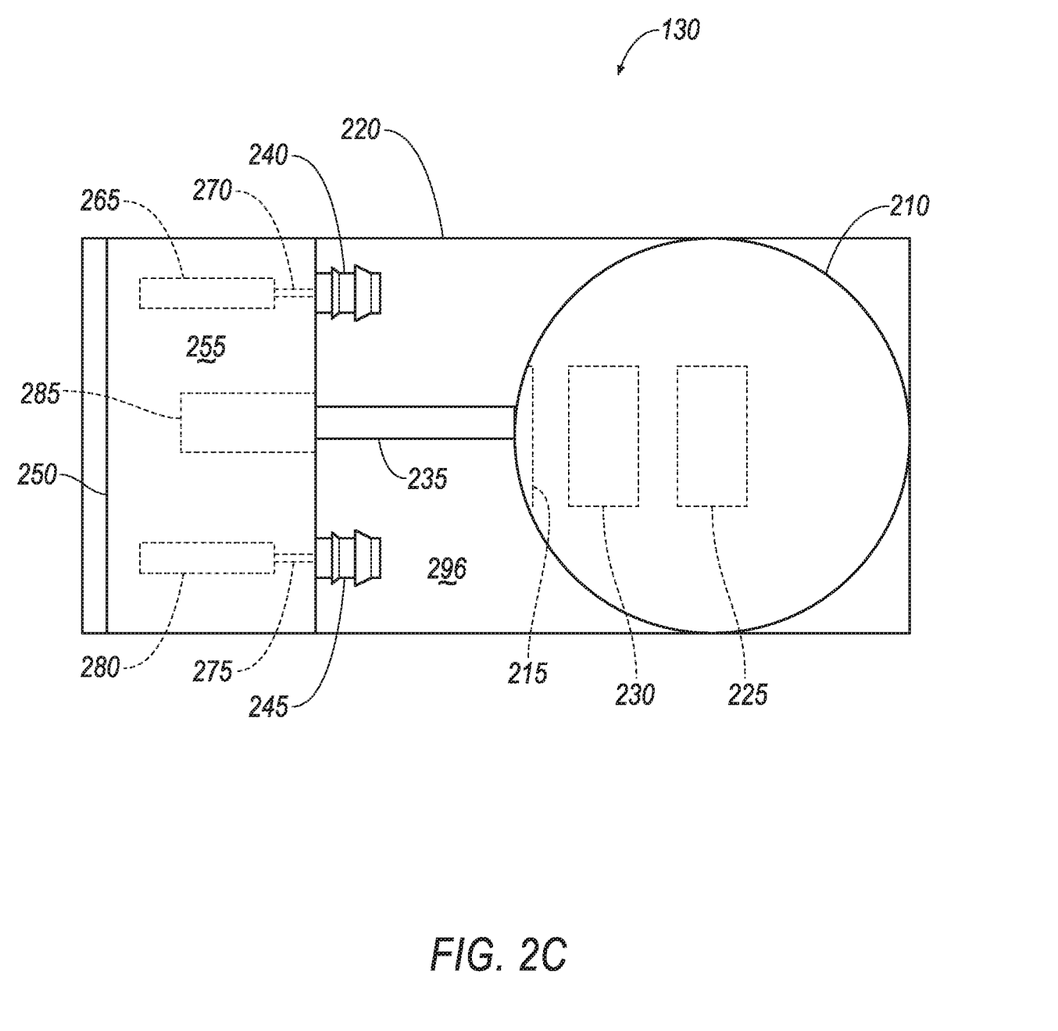
FIG. 2C is a diagram showing a top view of the sensor assembly with the contacting cleaner in a contacting position.

FIGS. 2A-2C show example LIDAR sensor 130 including a base 220, an excitation source 230, and a cover 210 having a window 215. The excitation source 230 may transmit an electro-magnetic beam such as a laser beam through the window 215 to an area surrounding the LIDAR sensor 130. The LIDAR sensor 130 may include a receiver that receives reflections of the transmitted electro-magnetic beams. The cover 210 may be formed of plastic, metal, etc. The cover 210 may protect the excitation source and/or other electronic components from environmental influences such as dirt, dust, rain, wind, etc. The window 215 may have a flat, round, etc. shape. The windows 215 may be formed of glass, plastic, etc. The windows 215 may include a lens, e.g., to focus electro-magnetic beams. The base 220 may have a bottom 295 and a top 296. The cover 210 may be mounted to the base 220 top 296.

As shown in FIGS. 2A-2C, a rotational LIDAR sensor 130 may include a rotational actuator 225, e.g., an electric motor, to move, e.g., rotate, the excitation source 230 relative to the base 220. In an example, the rotational actuator 225 may rotate the excitation source 230 about an axis A1 perpendicular to the base 220 top 296, and may provide a 360-degree horizontal field of view of an area around the LIDAR sensor 130. In one example, the excitation source 230, the cover 210, and the window 215 may rotate about the axis A1.

In order to provide data, a window 215 of a LIDAR sensor 130 may allow the transmitted electro-magnetic beams and received reflections of the transmitted radiations to pass through the window 215. Various conditions may cause a window 215 blockage, e.g., attenuating (weakening) the transmitted radiations and/or reflections thereof when passing through the window 215. For example, an object detection operation of a LIDAR sensor 130 may be impaired upon a blockage of the LIDAR sensor 130 window 215. In one example, dirt, dust, etc., on an exterior surface of the LIDAR sensor 130 window 215 can cause a blockage of the LIDAR sensor 130. For example, the computer 110 may be programmed to activate a non-autonomous mode of the vehicle 100 upon determining that a LIDAR sensor 130 cannot provide object data, e.g., due to a blockage of the LIDAR sensor 130.

The LIDAR sensor 130 may include a sensor 130 base 220, a sensor 130 cover 210 including a window 215, a contacting cleaner, e.g. a wiper 235, brush, sponge, etc., and a contactless cleaner, e.g., an air nozzle 240, a fluid spray nozzle 245, etc. The cover 210 may be rotatably mounted to the base 220. The system further includes a computer 110 that is programmed to actuate the contactless cleaner. The processor is further programmed to then actuate the contacting cleaner upon determining that opacity of the window 215 exceeds a predetermined threshold, e.g., an opacity threshold of 20%, after actuation of the contactless cleaner.

Opacity is a measure of the degree to which electromagnetic radiation such as the radiation emitted by the sensor 130 penetrates the window 215. An opacity may have a numerical quantity between 0% (zero) and 100%. Zero percent opacity may be associated with a transparent material, whereas 100% opacity may be associated with, e.g., a blocked window 215, that prevents a radiation from passing through the given medium. An increased opacity of the window 215, e.g., because of dust, dirt, etc., may impair sensor 130 operation. For example, the windows 215 covered with dirt may lack an ability to detect objects in the sensor 130 field of view. In one example, the computer 110 may be programmed to determine the opacity of the window 215 based on radiation received via the LIDAR sensor 130 electro-magnetic receiver. For example, the computer 110 may determine that the window 215 is blocked, e.g., when the window 215 opacity exceeds a predetermined threshold, e.g., 30%. In another example, the computer 110 may be programmed to determine that the window 215 is blocked upon determining that the window 215 opacity has been greater than the predetermined threshold for at least a predetermine minimum time duration, e.g., 5 seconds.

A contactless cleaner in the context of present disclosure includes a cleaning mechanism that in normal operation does not physically touch the window 215 and/or cover 210. For example, an air nozzle 240 and/or a fluid spray nozzle 245 may direct a flow of a gas such as air and/or a fluid such as a washer fluid to the window 215 while lacking a physical contact to the window 215. A contacting cleaner in the context of present disclosure includes a cleaning mechanism that may, in at least one of its possible positions, physically contact the window 215. For example, a wiper 235 may touch the window 215 surface.

As described above, the cover 210 is rotationally mounted to the sensor 130 base 220. Thus, physical contact of a contacting cleaner with the window 215 and/or the cover 210 may affect a rotational speed of the cover 210 relative to the base 220. On the other hand, a change in a rotational speed of the cover 210 may affect the sensor 130 operation, e.g., an ability of the sensor 130 to detect objects in a sensor 130 field of view. Thus, in one example, the computer 110 may be programmed to actuate a contactless cleaner as a first cleaning measure to prevent an influence on the sensor 130 operation. In this example, the computer 110 may be programmed to then, as a second cleaning measure, actuate a contacting cleaner upon determining that the contactless cleaner may lack an ability to clean the window 215. For example, the computer 110 may be programmed to determine that the contactless cleaner lacks an ability to clean the window 215, when, e.g., cleaning the window 215 with the contactless cleaner for at least a predetermined time interval has not reduced the opacity of the window 215 below a predetermined threshold.

Due to the physical contact, a contacting cleaner may affect, e.g., slow down, a rotational movement of the cover 210 and/or the excitation source 230. Thus, advantageously, by first actuating a contactless cleaner, a likelihood of actuating the contacting cleaner may be reduced. In other words, in cases that the actuation of a contactless cleaner resolves the window 215 blockage, then the contacting cleaner need not be actuated.

The LIDAR sensor 130 may include a cleaning arm 250 that is mounted to the top surface 296 of the sensor 130 base 220. The contactless and the contacting cleaners may be mounted to, e.g., a side surface 290 of, the cleaning arm 250. The cleaning arm 250 may have a solid rectangular, cylindrical, semi-cylindrical, or some other shape. The cleaning arm 250 may have a longitudinal axis A2 that may be parallel to the longitudinal axis A1 of the cover 210. The cleaning arm 250 may have a top surface 255 and a bottom surface 260. The cleaning arm 250 bottom 260 may be mounted to the sensor 130 base 220 top surface 296. In one example, the LIDAR sensor 130 may include the cleaning arm 250. Alternatively, the cleaning arm 250 may be included as a part of the vehicle 100 body or may be as a part of a separate apparatus mounted to, e.g., vehicle 100 roof 105.

In one example, the contactless cleaner includes an air nozzle 240 directed to the window 215 and mounted to the cleaning arm 250. The air nozzle 240 may be fluidly coupled, e.g., via an air hose 270, to an air pressure source such as an electrical air blower, an air compressor, a compressed air capsule, etc. The computer 110 may be programmed to actuate an actuator 265 such as an electric solenoid valve, to open a flow of air to the air nozzle 240 via the air hose 270. Thus, the flow of air from the air nozzle 240 may remove dust, dirt, etc., away from the window 215 surface. Additionally or alternatively, the computer 110 may be programmed to adjust the air flow by actuating the actuator 265 to partially open and/or close the flow of air.

In another example, the contactless cleaner includes a fluid spray nozzle 245 directed toward the window 215. The fluid spray nozzle 245 may spray washing fluid onto the window 215 surface. The fluid spray nozzle 245 may be fluidly connected via a fluid hose 275 to a fluid reservoir, e.g., a washer fluid container that supplies washer fluid to a vehicle 100 front and/or rear window. Additionally or alternatively, the vehicle 100 may include a fluid container disposed on the vehicle 100 roof 105. The computer 110 may be programmed to actuate a washer actuator 280, e.g., a wash pump, to spray washer fluid onto the window 215 surface.

The computer 110 may be programmed to determine whether a cleaning of the sensor 130 window 215 is warranted based on the window 215 opacity. For example, the computer 110 may be programmed to periodically determine an opacity of the sensor 130 window 215 and determine that the window 215 cleaning is warranted when the opacity of the window 215 exceeds a predetermined threshold, e.g., 30%. Upon determining that the window 215 cleaning is warranted, the computer 110 may be programmed to actuate, e.g., a contactless cleaner.

In one example, the LIDAR sensor 130 includes a first and a second contactless cleaner. For example, as shown in FIGS. 2A-2C, the LIDAR sensor 130 may include an air nozzle 240 and a fluid spray nozzle 245. The air nozzle 240 may be directed toward the window 215 in a downward direction (e.g., toward the vehicle 100 roof 105). The fluid spray nozzle 245 may be directed toward the sensor 130 window 215 in an upward direction (e.g., away from the base 220).

In another example, the air nozzle 240 and the fluid spray nozzle 245 are directed toward the window 215 and in a downward direction, e.g., toward to the base 220.

In yet another example, the air nozzle 240 and/or the fluid spray nozzle 245 are directed perpendicularly toward the window 215, i.e., longitudinal axes of the nozzles 240, 245 may be perpendicular to the axis A1. The computer 110 may be programmed to actuate the first contactless cleaner, and then actuate the second contactless cleaner upon determining that the opacity of the window 215 exceeds a predetermined threshold after actuation of the first contactless cleaner.

In another example, the computer 110 is programmed to actuate the second contactless cleaner upon determining that the opacity of the window exceeds a predetermined threshold after actuation of the first contactless cleaner for a predetermined time. For example, the computer 110 may be programmed to actuate the fluid spray nozzle 245 after determining that the opacity of the window 215 exceeds a predetermined threshold after actuation of the air nozzle 240 for a predetermine time, e.g., 5 seconds.

As explained above, a contacting cleaner may include a wiper 235. The wiper 235 may be moveably mounted to the cleaning arm 250. For example, the wiper 235 me be mechanically coupled to an electromechanical actuator 285 that is mounted to the cleaning arm 250. The contacting cleaner, e.g., the wiper 235, may have a contactless position (see FIGS. 2A-2B) and a window contacting position (see FIG. 2C). The wiper 235 physically touches the window 215 and/or the cover 210 in the window contacting position.

The computer 110 may be further programmed to actuate the electromechanical actuator 285 to move the wiper 235, e.g., between the window contacting position and the contactless position. In one example, the wiper 235 moves along a line A3 when moving between the contactless and window contacting positions. The line A3 may be parallel to the base 200 top 296. The wiper 235 may include a blade and/or brush formed of rubber, plastic, etc., that touches the window 215 in the window contacting position. Thus, when actuated by the computer 110, the wiper 235 may move relative to the cleaning arm 250.

In another example (not shown in Figures), the electromechanical actuator 285 may move the cleaning arm 250 relative to the base 220, i.e., the electromechanical actuator 285 may moveably couple the cleaning arm 250 and the base 220. Thus, in this example, the computer 110 may be programmed to move the cleaning arm 250 to move the wiper 235 from a contactless position to a window contacting position and vice versa.

In one example, the computer 110 is programmed to actuate the contacting cleaner based at least in part on a rotational position of the window 215. For example, the computer 110 may be programmed to actuate the wiper 235 to move to the window contacting position upon determining that the window 215 is positioned in front of the wiper 235. "The window 215 is positioned in front of the side surface 290" may, in one example, mean that the window 215 is substantially parallel to the side surface 290 and is disposed between the axis A1 and the side surface 290. The cover 210 may be formed of metal or any other material that may wear the wiper 235. Thus, advantageously, that may prevent the wiper 235 from touching the cover 210. In this example, the computer 110 may be programmed to periodically move the wiper 235 between the contactless and the window contacting positions based at least on a rotational speed of the window 215.

The wiper 235 in the contacting position may cause friction between the wiper 235 blade and the window 215 that may reduce a rotational speed of the cover 210. The computer 110 may be further programmed to determine a change in the rotational speed of the cover 210 upon actuation of the contacting cleaner. The computer 110 may be further programmed to cause an adjustment to interpretation of data from the sensor 130 according to the changed rotational speed. For example, the computer 110 may be programmed to determine object data, e.g., location of other vehicles, based at least in part on the rotational speed of the cover 210 and/or the excitation source 230. Thus, the computer 110 may be programmed to take into account the change of the excitation source 230 rotational speed, and interpret the data from the sensor 130 based on the changed rotational speed.

Processing

Figure 3A:
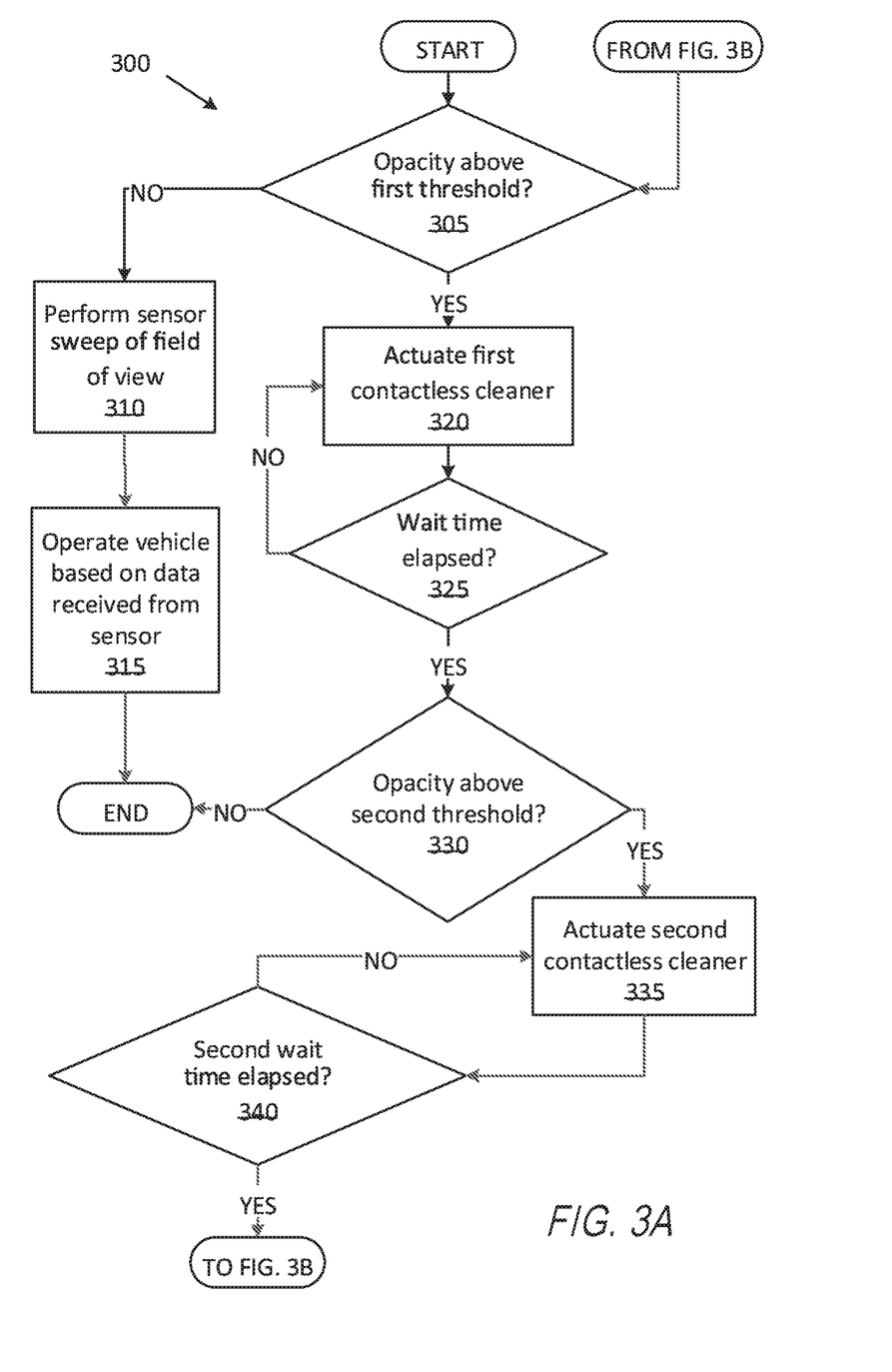
FIGS. 3A-3B are a flowchart of an exemplary process for operating the sensor assembly.
Figure 3B:
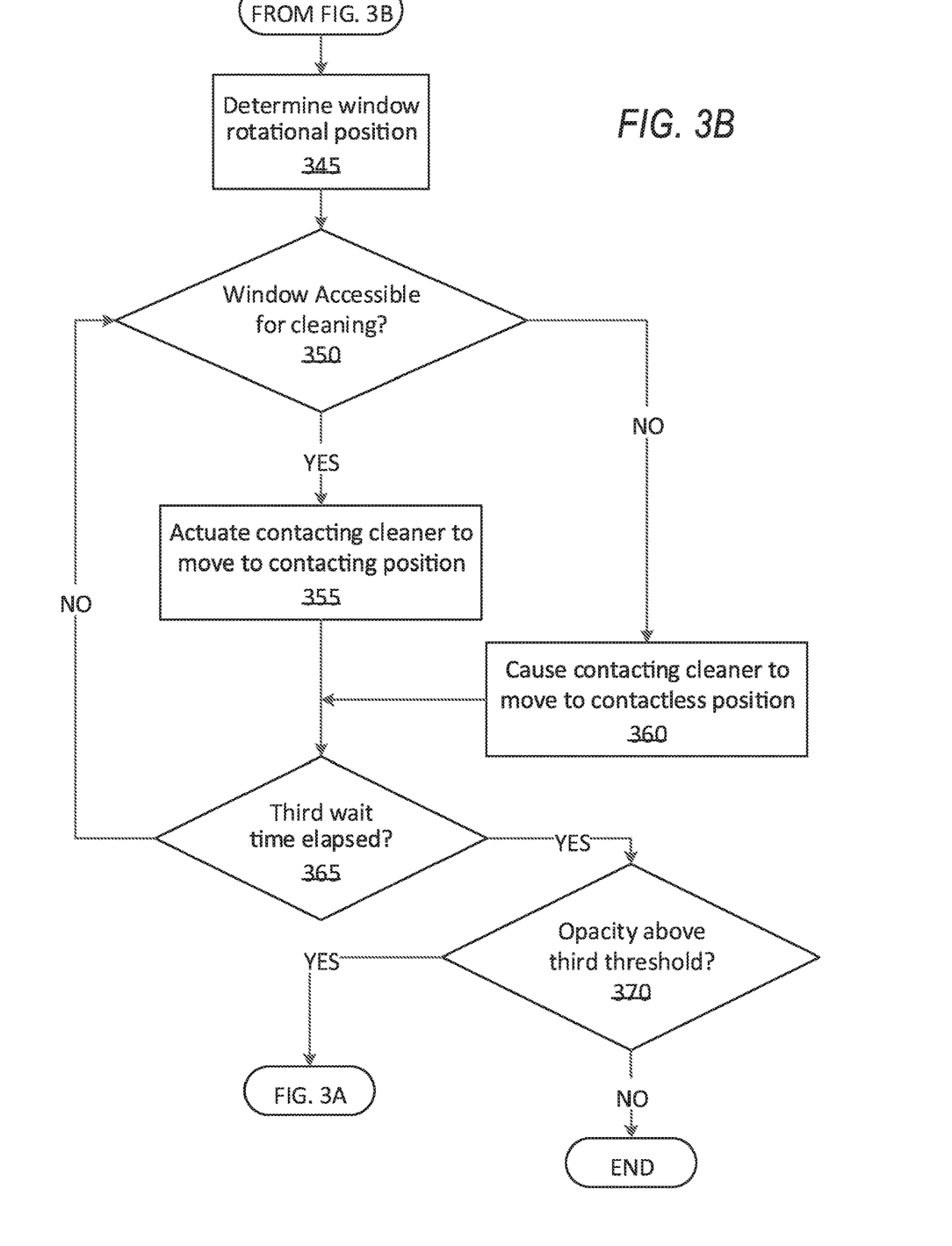

FIGS. 3A-3B are a flowchart of an example process 300 for operating a sensor 130. For example, the computer 110 may be programmed to execute blocks of the process 300.

The process 300 begins in a decision block 305, in which the computer 110 determines whether an opacity of the sensor 130 window 215 exceeds a first opacity threshold, e.g., 30%. In one example, the computer 110 may be programmed to determine the opacity of the window 215 based on the received data from the sensor 130 electromagnetic receiver. If the computer 110 determines that the opacity of the window 215 exceeds the first opacity threshold, e.g., because of dust on the window 215, then the process 300 proceeds to a block 320; otherwise the process 300 proceeds to a block 310.

In the block 310, the computer 110 performs actuates the sensor 130 to sweep a field of view. In one example, the computer 110 actuates the sensor 130 rotational actuator 225 to rotate the excitation source 230 and/or cover 210 about the axis A1 to collect data from the field of view of the sensor 130.

Next, in a block 315, the computer 110 operates the vehicle 100 based on data including data received from the sensor 130. The computer 110 may be programmed to operate the vehicle 100 in an autonomous or semi-autonomous mode. For example, the computer 110 may actuate vehicle 100 braking actuators 120 based on the received object data. Following the block 315 the process 300 ends, or alternatively returns to the decision block 305, although not shown in FIG. 3A.

In the block 320, the computer 110 actuates a first contactless cleaner. For example, the computer 110 may be programmed to actuate the air nozzle 240 to blow air to the window 215. Additionally, the computer 110 may be programmed to deactivate a vehicle 100 operation that is based on the sensor 130 data. For example, the computer 110 may be programmed to deactivate a semi- or full autonomous mode and to activate a non-autonomous mode. Additionally, the computer 110 may be programmed to transmit a message to the HMI 140 indicating that a vehicle 100 autonomous and/or semi-autonomous operation is deactivated due to a sensor 130 blockage.

Next, in a decision block 325, the computer 110 determines whether a predetermined first wait time, e.g., 5 seconds, has elapsed since the computer 110 actuated the first contactless cleaner. If the computer 110 determines that the first wait time has elapsed, then the process 300 proceeds to a decision block 330; otherwise the process 300 returns to the block 320.

In the decision block 330, the computer 110 determines whether the opacity of the window 215 exceeds a second opacity threshold, e.g., 20%. In other words, the computer 110 determines whether the window 215 is cleaned, upon cleaning the window 215 using the first contactless cleaner for a duration of the first wait time. If the computer 110 determines that the opacity of the window 215 exceeds the second opacity threshold, then the process 300 proceeds to a block 335; otherwise the process 300 ends, or alternatively, returns to the decision block 305, although not shown in FIG. 3A.

In the block 335, the computer 110 actuates a second contactless cleaner. For example, the computer 110 may be programmed to actuate the fluid spray nozzle 245 by actuating the washer actuator 280. Additionally, the computer 110 may be programmed to actuate the first contactless cleaner in addition to the second contactless cleaner, e.g., the computer 110 may be programmed to actuate the air nozzle 240 and the fluid spray nozzle 245 simultaneously. Here should be noted that this block may be applicable when the sensor 130 includes multiple contactless cleaners.

Next, in a decision block 340, the computer 110 determines whether a predetermined second wait time, e.g., 3 seconds, has elapsed since the computer 110 actuated the second contactless cleaner. If the computer 110 determines that the second wait time has elapsed, then the process 300 proceeds to a block 345 (see FIG. 3B); otherwise the process 300 returns to the block 335.

With reference to FIG. 3B, in the block 345, the computer 110 determines a rotational position of the window 215 and/or the cover 210. For example, the computer 110 may be programmed to determine the window position in units of radians. The rotational position may be determined relative to a reference position, e.g., 0 (zero) radian position may be defined as where the window 215 faces the cleaning arm 250 and the line A3 passes through a center of the window 215.

Next, in a decision block 350, the computer 110 determines whether the window 215 is accessible by the contacting cleaner. For example, the computer 110 may be programmed to determine that the window 215 is accessible by the wiper 235 upon determining that the rotational position of the window 215 is within a rotational position interval, e.g., −0.2 radian to 0.2 radian. In other words, the computer 110 determines whether the window 215 is where it can be physically touched by the contacting cleaner upon the contacting cleaner movement to the contacting position. If the computer 110 determines that the window 215 is accessible by the contacting cleaner, then the process 300 proceeds to a block 355; otherwise the computer 110 proceeds to a block 360.

In the block 355, the computer 110 actuates the contacting cleaner to move to the contacting position. For example, the computer 110 can actuate the wiper 235 to move away from the cleaning arm 250 to the contacting position, i.e., touching the window 215 surface. The computer 110 may be further programmed to deactivate the sensor 130 excitation source 230 upon actuation of the contacting cleaner, e.g., because the window 215 may be blocked by the contacting cleaner in the window contacting position. In one example, the computer 110 may be programmed to prevent an actuation of the wiper 235, if the wiper 235 is already in the contacting position.

In the block 360, the computer 110 actuates the contacting cleaner to move to the contactless position. For example, the computer 110 actuates the wiper 235 to move away from the window 215 and/or cover 210 to the contactless position. In one example, the computer 110 may be programmed to prevent an actuation of the wiper 235, if the wiper 235 is already in the contactless position.

Next, in a decision block 365, the computer 110 determines whether a predetermined third wait time, e.g., 2 seconds, has elapsed since the computer 110 determined that the second wait time has elapsed. If the computer 110 determines that the third wait time has elapsed, then the process 300 proceeds to a decision block 370; otherwise the process 300 returns to the decision block 350.

In the decision block 370, the computer 110 determines whether the opacity of the window 215 exceeds a third opacity threshold, e.g., 10%. In one example, the computer 110 may be programmed to repeat the process of cleaning the window 215 in multiple steps using the first and second contactless cleaners and then using the contacting cleaner, if the cleaning process has not cleaned the window 215. If the computer 110 determines that the window 215 opacity exceeds the third opacity threshold, then the process 300 proceeds to the decision block 305; otherwise the process 300 ends, or alternatively, returns to the decision block 305 (see FIG. 3A).

The article "a" modifying a noun should be understood as meaning one or more unless stated otherwise, or context requires otherwise. The phrase "based on" encompasses being partly or entirely based on.

Computing devices as discussed herein generally each include instructions executable by one or more computing devices such as those identified above, and for carrying out blocks or steps of processes described above. Computer-executable instructions may be compiled or interpreted from computer programs created using a variety of programming languages and/or technologies, including, without limitation, and either alone or in combination, Java™, C, C++, Visual Basic, Java Script, Perl, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media. A file in the computing device is generally a collection of data stored on a computer readable medium, such as a storage medium, a random access memory, etc.

A computer-readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH, an EEPROM, any other memory chip or cartridge, or any other medium from which a computer can read.

With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of systems and/or processes herein are provided for the purpose of illustrating certain embodiments, and should in no way be construed so as to limit the disclosed subject matter.

Accordingly, it is to be understood that the present disclosure, including the above description and the accompanying figures and below claims, is intended to be illustrative and not restrictive. Many embodiments and applications other than the examples provided would be apparent to those of skill in the art upon reading the above description. The scope of the invention should be determined, not with reference to the above description, but should instead be determined with reference to claims appended hereto and/or included in a non-provisional patent application based hereon, along with the full scope of equivalents to which such claims are entitled. It is anticipated and intended that future developments will occur in the arts discussed herein, and that the disclosed systems and methods will be incorporated into such future embodiments. In sum, it should be understood that the disclosed subject matter is capable of modification and variation.

What is claimed is:

1. A system, comprising: a computer that includes a processor and a memory, the memory storing instructions such that the processor is programmed to:
   actuate, first, a contactless cleaner upon determining that an opacity of a window of a cover of a sensor exceeds a first predetermined threshold, and, then, after actuation of the contactless cleaner and upon determining that opacity of the window exceeds a second predetermined threshold that is different than the first predetermined threshold, a contacting cleaner;
   determine a change in a rotational speed of the cover upon actuation of the contacting cleaner; and
   cause an adjustment to interpretation of data from the sensor according to the changed rotational speed.

2. The system of claim 1, wherein the contactless cleaner includes an air nozzle directed to the window or a cleaning fluid spray nozzle directed to the window.

3. The system of claim 1, wherein the contacting cleaner includes a wiper mechanically connected to an actuator, and the processor is further programmed to actuate the actuator to move the wiper to a window contacting position.

4. The system of claim 1, wherein the contacting cleaner has a contactless position and a window contacting position, and the contacting cleaner physically touches the window in a window contacting position.

5. The system of claim 4, wherein an electromechanical actuator is mechanically coupled to the contacting cleaner, wherein the processor is further programmed to actuate the electromechanical actuator to move the contacting cleaner from the contactless position to the window contacting position.

6. The system of claim 1, wherein the contactless cleaner is a first contactless cleaner, and the processor is further programmed to:
   actuate the first contactless cleaner; and
   then actuate a second contactless cleaner upon determining that the opacity of the window exceeds a third predetermined threshold after actuation of the first contactless cleaner.

7. The system of claim 6, wherein the processor is further programmed to actuate the second contactless cleaner upon determining that the opacity of the window exceeds the first predetermined threshold after actuation of the first contactless cleaner for a predetermined time.

8. The system of claim 1, wherein the contactless and the contacting cleaners are mounted to the cleaning arm that is mounted to a sensor base.

9. The system of claim 1, wherein the processor is further programmed to deactivate a sensor excitation source upon actuation of the contacting cleaner.

10. The system of claim 1, wherein the processor is further programmed to actuate the contacting cleaner based at least in part on a rotational position of the window.

11. A system, comprising:
   a sensor base;
   a sensor cover including a window and rotatably mounted to the base;
   a contacting cleaner and a contactless cleaner; and
   a processor programmed to:
      actuate, first, the contactless cleaner and, then, upon determining that opacity of the window exceeds a predetermined threshold after actuation of the contactless cleaner, the contacting cleaner;
      determine a change in a rotational speed of the cover upon actuation of the contacting cleaner; and
      cause an adjustment to interpretation of data from a sensor according to the changed rotational speed.

12. The system of claim 11, wherein the contacting cleaner has a contactless position and a window contacting position, and the contacting cleaner physically touches the window in a window contacting position.

13. The system of claim 12, further comprising an electromechanical actuator mechanically coupled to the contacting cleaner, wherein the processor is further programmed to actuate the electromechanical actuator to move the contacting cleaner from the contactless position to the window contacting position.

14. The system of claim 11, wherein the contactless cleaner is a first contactless cleaner and the system further includes a second contactless cleaner, and the processor is further programmed to:
   actuate the first contactless cleaner; and
   then actuate the second contactless cleaner upon determining that the opacity of the window exceeds a predetermined threshold after actuation of the first contactless cleaner.

15. The system of claim 14, wherein the processor is further programmed to actuate the second contactless cleaner upon determining that the opacity of the window exceeds a predetermined threshold after actuation of the first contactless cleaner for a predetermined time.

16. The system of claim 11, further comprising a cleaning arm mounted to the sensor base, wherein the contactless and the contacting cleaners are mounted to the cleaning arm.

17. The system of claim 11, wherein the processor is further programmed to deactivate a sensor excitation source upon actuation of the contacting cleaner.

* * * * *